United States Patent [19] [11] 4,108,998
Demerson et al. [45] Aug. 22, 1978

[54] FURO[3,4-B]QUINOLINE DERIVATIVES AND PHARMACEUTICAL COMPOSITIONS AND METHODS EMPLOYING THEM

[75] Inventors: Christopher A. Demerson, Montreal; Leslie G. Humber, Dollard des Ormeaux, both of Canada

[73] Assignee: American Home Products Corp., New York, N.Y.

[21] Appl. No.: 739,779

[22] Filed: Nov. 8, 1976

[51] Int. Cl.² .................. A61K 31/47; C07D 491/14
[52] U.S. Cl. .................. 424/258; 424/248.56; 260/288 A; 260/288 CF; 260/287 CF; 260/289 C; 544/126; 544/361; 260/283 SA
[58] Field of Search .................. 260/288 A, 288 CF; 424/258

[56] References Cited
U.S. PATENT DOCUMENTS
2,650,229 8/1953 Timmler et al. .............. 260/288 CF FOREIGN PATENT DOCUMENTS
1,022,940 3/1966 United Kingdom.

OTHER PUBLICATIONS
Queguiner, et al., Chemical Abstracts, v. 72, 132,579s (1970).
Godard, et al., Chemical Abstracts, v. 75, 20,328q (1971).
Haddadin et al., Chemical Abstracts, v. 81, 169,510Z (1974).

Primary Examiner—Donald G. Daus
Assistant Examiner—Diana G. Rivers
Attorney, Agent, or Firm—Adley F. Mandel

[57] ABSTRACT

Furo[3,4-b]quinoline derivatives, having both an alkyl substituent and an alkyl or alkylene amide substituent at position 3 are disclosed. The derivatives can be further substituted at positions 1 and 9. The furo[3,4-b]quinoline derivatives of this invention are useful antihypertensive and antimicrobial agents. Methods for the preparation and use of these derivatives are also disclosed.

22 Claims, No Drawings

FURO[3,4-B]QUINOLINE DERIVATIVES AND PHARMACEUTICAL COMPOSITIONS AND METHODS EMPLOYING THEM

BACKGROUND OF THE INVENTION (a) Field of the Invention

This invention relates to novel furo[3,4-b]quinoline derivatives, to processes for their preparation, to intermediates used for the process, to methods for using said derivatives and to pharmaceutically acceptable compositions of said derivatives.

The furo[3,4-b]quinoline derivatives possess valuable pharmacologic properties. For example, these derivatives are useful for treating hypertension and microbial infections in a mammal at dosages which do not elicit undesirable side effects. The combination of these pharmacologic properties together with a low order of toxicity render the furo[3,4-b]quinoline derivatives of the invention therapeutically useful.

(b) Description of the Prior Art

Only a rather limited number of reports dealing with furo[3,4-b]quinoline derivatives have been published. For example, some furo[3,4-b]quinolines that can be considered are: acridinic anhydride, see Hozer and V. Niementowski, J. Prakt Chem., 116, 45 and 50 (1927) and "Beilstein's Handbuch der Organischen Chemie, Vierte Auglage", 11, 27, p. 311; substituted and unsubstituted furo[3,4-b]quinolin-1(3H)-ones, see E. A. Fehnel, et al., J. Org. Chem., 23, 1996 (1958), A. Godard et al., Bull. Soc. Chem. Fr., 906 (1971), G. Quequiner and A. Godard, C.R. Acad. Sci. Series C, 269, 1646 (1969) and L. Neilands and G. Vanags, Khim. Geterotskikl. Soedin. Akad, Naulk, Latv, SSR, 1965 (6), p. 884–888 (CA 64 12638 h); furo[3,4-b]quinolin-3-(1H)-one, see G. Quequiner and A. Godard, cited above; 1-methyl-2-carboxy-3-hydroxymethyl-4-(1H)-guinoline lactone, see J. R. Prince, Amst. J. Sci. Research 2A, 249 (1949); and 1,1,3,3-tetraalkyl-1,3-dihydrofuro[3,4-b]quinolines, see I. K. Korobitsyna et al., Zhur, Obshchei Khim., 31, 836 (1961). The compounds of the prior art are readily distinguished from the compounds of the present invention by existing at different oxidation states as well as having different substituents on the furo[3,4-b]quinoline nucleus.

SUMMARY OF THE INVENTION

The compounds of this invention are represented by formula I

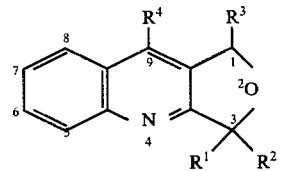

in which $R^1$ is lower alkyl; $R^2$ is lower alkyl or a radical of formula

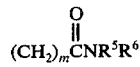

wherein m is an integer from 1 to 5 and $R^5$ and $R^6$ each is lower alkyl; $R^3$ is hydrogen, lower alkyl or a radical of formula $(CH_2)_nNR^7R_8$ wherein n is an integer from 1 to 6 and $R^7$ and $R^8$ each is lower alkyl; and $R^4$ is hydrogen, chloro, bromo, p-toluenesulfonyl or a radical of formula Y-X wherein Y is O or NH and X is lower alkyl, phenyl, 2,2,6,6-tetramethyl-4-piperdinyl or a radical of formula Z-$R^9$ wherein Z is lower alkylene or hydroxy(lower)alkylene and $R^9$ is phenyl, 4-morpholinyl, 4-methyl-1-piperazinyl, 1-pyrrolidinyl, 2-oxo-1-pyrrolidinyl, 3-pyridyl or a radical of formula $NR^{10}R^{11}$ wherein $R^{10}$ and $R^{11}$ each is hydrogen, lower alkyl or hydroxy(lower)alkyl.

A preferred group of compounds of this invention is represented by formula I in which $R^1$ is lower alkyl; $R^2$ is lower alkyl; $R_3$ is hydrogen or a radical of formula $(CH_2)_nNR^7R^8$ wherein n is an integer form 1 to 6 and $R^7$ and $R^8$ each is lower alkyl; and $R^4$ is hydrogen, chloro, bromo, p-toluenesulfonyl or a radical of formula Y-X wherein Y is O and X is phenyl or a radical of formula Z-$R^9$ wherein Z is lower alkylene or hydroxyl(lower)alkylene and $R^9$ is a radical of formula $NR^{10}R^{11}$ wherein $R^{10}$ and $R^{11}$ each is hydrogen or lower alkyl, or Y is NH and X is 2,2,6,6-tetramethyl-4-piperidinyl or a radical of formula Z-$R^9$ wherein Z is lower alkylene or hydroxy(lower)alkylene and $R^9$ is phenyl, 4-morpholinyl, 4-methyl-1-piperazinyl, 1-pyrrolidinyl, 3-pyridyl or a radical of formula $NR^{10}R^{11}$ wherein $R^{10}$ and $R^{11}$ each are lower alkyl or hydroxy(lower)alkyl; with the proviso that when $R^1$ and $R^2$ are as defined herein and $R^3$ is a radical of formula $(CH_2)_nNR^7R^8$ wherein n, $R^7$ and $R^8$ are as defined herein then $R^4$ is hydrogen, chloro or bromo.

Also included are the therapeutically acceptable acid addition salts of the basic compounds of formula I.

The compounds of formula I are prepared by a process comprising: oxidizing a compound of formula II

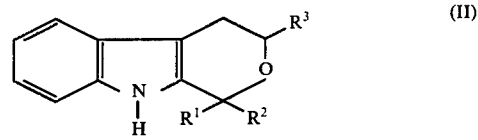

in which $R^1$, $R^2$ and $R^3$ are as defined herein with an agent known to be effective for cleaving an indolic 2,3-double bond to obtain the corresponding compound of formula V

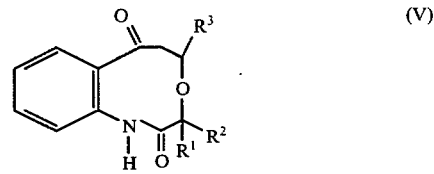

in which $R^1$, $R^2$ and $R^3$ are as defined herein;

cyclizing said last-named compound of formula V in the presence of a proton acceptor to obtain the corresponding compound of formula VI

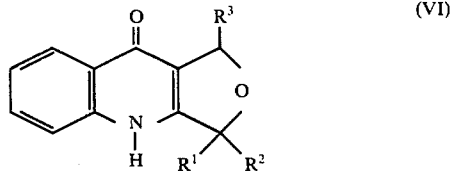

in which $R^1$, $R^2$ and $R^3$ are as defined herein; and followed by transformation of the latter compound of formula VI to said compounds of formula I by methods described herein.

More specifically, the transformation of the compound of formula VI to said compound of formula I comprises:

(a) reacting said compound of formula VI with p-toluenesulfonyl chloride or bromide in the presence of a proton acceptor to obtain the corresponding compound of formula I in which $R^1$, $R^2$ and $R^3$ are as defined herein and $R^4$ is p-toluenesulfonyl; or (b) reacting said compound of formula VI with a compound of formula halogen-X in which the halogen is selected from chlorine or bromine and X is lower alkyl, 2,2,6,6-tetramethyl-4-piperidinyl or a radical of formula $Z$-$R^9$ wherein Z and $R^9$ are as defined herein in the presence of a proton acceptor to obtain the corresponding compound of formula I in which $R^1$, $R^2$ and $R^3$ are as defined herein and $R^4$ is a radical of formula Y-X wherein Y is O and X is lower alkyl, 2,2,6,6-tetramethyl-4-piperidinyl or a radical of formula $Z$-$R^9$ wherein Z and $R^9$ are as defined herein; or (c) reacting said compound of formula VI with a halogenating agent to obtain the corresponding compound of formula I in which $R^1$, $R^2$ and $R^3$ are as defined herein and $R^4$ is chloro or bromo, and reacting said last-named compound of formula I with Raney nickel in the presence of an alkali hydroxide to obtain the corresponding compound of formula I in which $R^1$, $R^2$ and $R^3$ are as defined herein and $R^4$ is hydrogen; or (d) reacting said compound of formula I in which $R^1$, $R^2$ and $R^3$ are as defined herein and $R^4$ is bromo or chloro with a compound of formula H—Y—X wherein Y is NH and X is as defined herein or Y is O and X is phenyl to obtain the corresponding compound of formula I in which $R^1$, $R^2$ and $R^3$ are as defined herein and $R^4$ is a radical of formula Y-X wherein Y is NH and X is as defined herein or Y is O and X is phenyl.

Another aspect of this invention involves a method of treating hypertension in a mammal which comprises administering to said mammal an antihypertensive effective amount of a compound of formula I or a therapeutically acceptable salt thereof.

Still another aspect of this invention involves a method of treating microbial infections in a mammal which comprises administering to said mammal an antimicrobial effective amount of a compound of formula I or a therapeutically acceptable salt thereof.

Still another aspect involves a pharmaceutical composition comprising a compound of formula I or a therapeutically acceptable salt thereof, and a pharmaceutically acceptable carrier therefor.

DETAILED DESCRIPTION OF THE INVENTION

The term "lower alkyl" as used herein contemplates straight branched chain alkyl radicals containing from one to six carbon atoms and branched chain alkyl radicals containing three to four carbon atoms and includes methyl, ethyl, propyl, isopropyl, butyl, isobutyl, pentyl, hexyl and like.

The terms "lower alkylene" and "hydroxy(lower)alkylene" as used herein contemplates a divalent organic radical derived from both straight and branched chain aliphatic and hydroxy-aliphatic hydrocarbons, respectively, containing from one to six carbon atoms by removal of two H atoms and includes methylene, 2-hydroxyethylene, 1-methylpropylene, 3-hydroxy-2-ethylpropylene, 2-butylethylene and the like.

The basic compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, ether (i.e., diethyl ether) or an ethanol-ether mixture. These salts, when administered to a mammal, posses the same pharmacologic activities as the correspondingg bases. For many purposes it is preferable to administer the salts rather than the base compounds. Examples of salts are those with organic acids, e.g. acetic, lactic, succinic, benzoic, salicyclic, maleic, methanesulfonic or toluenesulfonic acid, as well as polymeric acids such as tannic acid or carboxymethyl cellulose, and salts with inorganic acids, for example, phosphoric acid, sulfuric acid or hydrohalic acids, e.g. hydrochloric acid and hydrobromic acid. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included within the scope of this invention are the isomers of the compounds of formula I resulting from the asymmetric centers contained therein.

ANTIHYPERTENSIVE ACTIVITY

The antihypertensive effect of the compounds of formula 1 or therapeutically acceptable acid addition salts thereof is demonstrated in standard pharmacological tests. For example, in tests conducted in the spontaneously hypertensive rat (SHR) such as described by R. Tabei, et al., Clin. Pharmacol. Therap. II, 269 (1970) or I. Varva, et al., Can. J. Physiol. Pharmacol., 51, 727 (1973). More Specifically exemplified, a testing method such as described in the latter publication show that the preferred compounds 9-[[3-(dimethylamino)propyl]amino]-3,3-dimethyl-1,3-dihydrofuro[3,4-b]quinoline (Example 26), 3,3-dimethyl-9-[[3-(diethylamino)-2-hydroxypropyl]amino] -1,3-dihydrofuro[3,4-b]quinoline (Example 29), 3,3-dimethyl-9-[[3-di-2-ethanolamino)propyl]amino]-1,3-dihydrofuro[3,4-b]quinoline (Example 33), 3,3-dimethyl-9-[(2,2,6,6,-tetramethyl-4-piperidinyl)amino]-1,3-dihydrofuro[3,4-b]quinoline (Example 35) and 1,3-dihydro-3,3-dimethyl-9-[2-(dimethylamino)ethoxyl]furo[3,4-b]quinoline (Example 46) cause a notable blood pressure decrease in the SHR at about four hours after a dose of 10-150 mg per kilogram body weight perorally.

When the compounds of formula I of this invention are used as antihypertensive agents in mammals e.g. rats, dogs and mice, they are used alone or in combination with pharmacologically acceptable carriers, the proportion of which is determined by the solubility and chemical nature of the compound, chosen route of administration and standard biological practice. For example, they are administered orally in solid form i.e. capsule or tablet. They may also be administered orally in the form of suspensions or solutions or they may be injected parenterally. For parenteral administration they may be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets may be uncoated or they may be coated by known techniques so as to delay disintegration and absorption in the gastrointentinal tract and thereby provide a sustained action over a longer period.

The aqueous suspensions of the invention contain the active ingredient in admixture with one or more non-toxic pharmaceutical excipients known to be suitable in the manufacture of aqueous suspensions. Suitable excipients are, for example, methyl-cellulose, sodium aliginate, gum acacia, lecithin and so forth. The aqueous suspensions may also contain one or more preservatives, one or more coloring agents, one or more flavouring agents and one or more sweetening agents.

Non-aqueous suspensions may be formulated by suspending the active ingredient in a vegetable oil, for example, arachic oil, olive oil, sesame oil, or coconut oil, or in a mineral oil, for example liquid paraffin, and the suspension may contain a thickening agent, for example beeswax, hard paraffin or cetyl alcohol. These compositions may also contain a sweetening agent, flavouring agent and antioxidant.

The dosage of the furo[3,4-b]quinoline derivatives of this invention as antihypertensive agents will vary with the form of administration and the particular compound chosen. Furthermore, it will vary with the particular host as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective antihypertensive amount of the compounds usually ranges from about 1.0 mg to about 500 mg per kilogram body weight per day, although as aforementioned variations will occur. However a dosage level that is in the range of from about 10 mg to about 300 mg per kilogram body weight per day is employed most desirably in order to achieve effective results.

ANTIMICROBIAL ACTIVITY

The compounds of formula I or a therapeutically acceptable salt thereof also exhibit utility as antimicrobial agents against a number of microorganisms, such as bacteria, fungi, mycobacteria and protozoa. The antimicrobial activity is demonstrated in standard tests, for example in those described in "Antiseptics, Disinfectants, Fungicides and Sterilization", G. F. Reddish, Ed., 2nd. ed., Lea and Febiger, Philadephia, 1957 or by D. C. Grove and W. A. Randell in "Assay Methods of Antibiotics", Med. Encycl. Inc., New York 1955.

The compounds are useful as antibacterial agents against a number of gram-positive and gram-negative microorganisms, such as Staphylocooccus pyogenes, both penicillin sensitive and penicillin resistant, *Streptococcus faecalis, Escheria coli, Aerobacter aerogenes, Salmonella pullorum, Pseudomonas aeruginosa* and *Serratia marcescens* and as antifungal agents against a number of pathogenic fungi, such as Candida albicans, Microsporum gypseum and *Trichophyton granulosum*. In addition, the compounds exhibit utility as antimycobaterial agents against a number of mycobacterium species, such as *Mycobacterium fortuitum, Mycobacterium photochromogene, Mycobacterium scotochromogene* and *Mycobacterium tuberculosis* as well as beng useful against a number of parasitic protozoa, for example, *trichomonas foetus* and Trichomonas Vaginalis.

When the compounds of this invention are employed as antimicrobial agents in a mammal they are administered in the same manner as described above for their use as antihypertensive agents.

The preferred dosage of the present therapeutic agents as antimicrobial agents is in the range of from about 50 mg to about 500 mg per kilogram body weight per day in order to achieve effective results.

In addition, the antibacterial or antifungal agents may be employed topically. For topical application they may be formulated in the form of solutions, creams, or lotions in pharmaceutically acceptable vehicles containing 0.1-5 percent, preferably 2 percent, by weight of the agent and may be administered topically to the infected area of the skin.

Also the antibacterial properties of the compounds of this invention can be utilized for washing equipment in hospitals, homes and farms, instruments used in medicine and bacteriology, clothing used in bacteriological laboratories, and floors, walls and ceilings in rooms in which a background free of gram-positive and gram-negative microorganisms, such as those listed above, is desired. When employed in this manner the compounds of this invention may be formulated in a number of compositions comprising the active compound and an inert material. In such compositions, while the compounds of formula I of this invention may be employed in concentrations as low as 500 p.p.m., from a practical point of view, it is desirable to use from about 0.10 percent by weight, to about 5 percent by weight or more.

The formulations that can be used to prepare antiseptic wash solutions of the compounds of this invention are varied and may readily be accomplished by standard techniques, see for example, "Remington's Practice of Pharmacy", E. W. Martin et al., Eds., 12th ed., Mack Publishing Company, Easton, Pa., 1961, pp. 1121-1150. In general, the compounds may be made up in stock solutions. They can also be formulated as suspensions in an aqueous vehicle. These make useful mixtures for decontaminating premises. Also, aqueous vehicles containing emulsifying agents, such as sodium lauryl sulfate, and relatively high concentrations, e.g. up to about 5 percent by weight, of the compounds may be formulated by conventional techniques.

PROCESS

For the preparation of the furo[3,4-b]quinoline derivatives of this invention, the preferred starting materials are the pyranoindoles of formula II

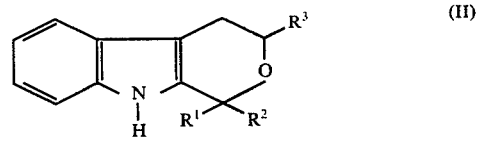

(II)

in which $R^1$, $R^2$ and $R^3$ are as defined herein. These starting materials are either known, for example, see U.S. Pat. No. 3,880,853, issued April 29, 1975, U.S. Pat.

No. 3,843,681, issued Oct. 22, 1974 and C. A. Demerson et al., J. Med. Chem., 18, 189 (1975), or they are obtained by the following process:

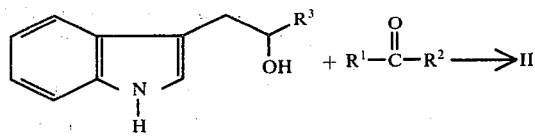

III    IV in which $R^1$, $R^2$ and $R^3$ are as defined herein.

With reference to the above scheme an appropriately substituted tryptophol of formula III is condensed with a keto compound of formula IV in the presence of a suitable acid catalyst, for example, the type of catalyst used in a Friedel-Crafts reaction to yield the starting material of formula II. Preferred catalysts are p-toluenesulfonic acid, boron trifluoride etherate or phosphorus pentoxide.

The starting material, the pyranoindole of formula II, is oxidized with a suitable oxidizing agent, whereupon the indole double bond is oxidatively cleaved to yield the corresponding 4,1-benzoxazonine of formula V

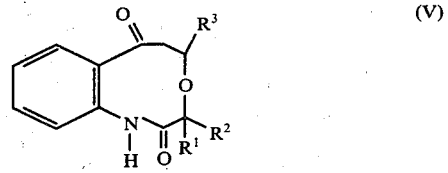

in which $R^1$, $R^2$ and $R^3$ are as defined herein. Suitable oxidizing agents are those known to be effective for cleaving the 2,3-double bond of an indole and include ozone, hydrogen peroxide, organic peracids, oxygen and sodium metaperiodate.

The oxidative cleavage of the indole double bond is well documented and a variety of methods are available. For example, these include ozonolysis, described by B. Witkop and J. Patrick, J. Amer. Chem. Soc., 74, 3855 (1972) and B. Witkop and S. Goodwin, J. Amer. Chem. Soc., 74, 337 (1953), hydrogen peroxide in the presence of ammonium molybdate, described by G. Clerc-Bory et al, Bull. Soc. France, 1229 (1955), oxidation by peracids, described by B. Witkop, J. Amer. Chem. Soc., 72, 1428 (1950), autoxidation, described by B. Witkop and J. Patrick, J. Amer. Chem. Soc., 73, 2196 (1951) and E. Winterfeldt, Liebigs Ann. Chem., 745, 23(1971) and sodium metaperiodate oxidation, described by L. J. Dolby and D. L. Booth, J. Amer. Chem. Soc., 88, 1049 (1966). The latter method using sodium metaperiodate oxidation is the method of choice for the oxidation of the starting material of formula II since it is facile and gives good yields.

In practising the oxidation (II → V) it is preferable to add a solution of the starting material of formula II in a solvent inert to the reactants, for example, tetrahydrofuran, dioxane or a lower alkanol, preferably methanol, ethanol or propanol, to a solution containing substantially 2 to 10 molar equivalents preferably 2 to 3 molar equivalents, of sodium metaperiodate in water. The time of the reaction can range from 1 hour to 60 hours, with the preferred range from 5 to 30 hours. The temperature of the reaction may range from 0° C to the boiling point of the reaction mixture, with the preferred temperature range being from 10° to 50° C. The compounds of formula V are isolated from the reaction mixture by conventional methods, for example, filtration, evaporation, extraction, chromatography and/or crystallization.

Thereafter, the 4,1-benzoxazonine of formula V is cyclized in the presence of a proton acceptor to obtain the corresponding compound of formula VI

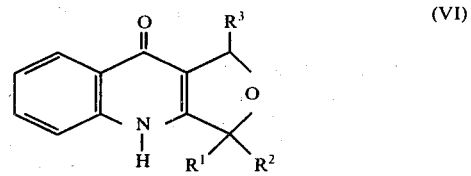

in which $R^1$, $R_2$ and $R_3$ are as defined herein. A variety of suitable organic and inorganic proton acceptors can be used for this cyclization. Suitable organic proton acceptors are selected from the class consisting of pyridine, N-methylmorpholine, triethylamine and the like. Practical and useful proton acceptors are those of the inorganic type; for example, sodium hydride; sodium amide; organo-lithium compounds, for instance, n-butyl lithium; or an alkali metal hydroxide, carbonate, bicarbonate, or alkoxide, for instance, potassium hydroxide, sodium hydroxide, potassium carbonate, sodium bicarbonate, sodium methoxide, sodium ethoxide, potassium t-butoxide and the like. Suitable inert solvents for the latter cyclization include water; lower alkanols, for example, methanol, ethanol and propanol; and di(lower)alkyl and cyclo(lower)alkyl ethers, for example diethyl ether, dioxane, tetrahydroguran and the like, or mixtures thereof. In a preferred embodiment, sodium hydride is the proton acceptor and tetrahydrofuran is the solvent. Convenient and practical and conditions for this cyclization are a temperature range from 0° C to the boiling point of the reaction mixture, preferably 10° to 50° C, for about ½ to 24 hours, preferably 1 to 5 hours. The compound of formula VI is separated from the reaction mixture by conventional methods, for instance, see examples herein.

The oxidation of the compound of formula II in which $R^1$ and $R^2$ are as defined herein and $R^3$ is a radical of formula $(CH_2)_n NR^7 R^8$ may also directly afford the corresponding compound of formula VI in which $R^1$ and $R^2$ are as defined herein and $R^3$ is a radical of formula $(CH_2)_n NR^7 R^8$. Thus, the compound of formula VI in which $R^3$ is a radical of formula $(CH_2)_n NR^7 R^8$ can be obtained directly without isolating the corresponding compound of formula V and reacting the latter compound with a proton acceptor.

In one aspect of this invention the compound of formula VI is readily converted to the corresponding compound of formula I in which $R^1$, $R^2$ and $R^3$ are as defined herein and $R^4$ is p-toluenesulfonyl. The p-toluenesulfonate of the compound of formula VI is prepared by reacting the compound of formula VI with at least one molar equivalent of p-toluene-sulfonyl chloride or bromide in the presence of an organic proton acceptor, preferably pyridine, triethylamine and the like. A particularly useful solvent is an excess of the organic proton acceptor. The reaction is maintained at a temperature of about −20° to 50° C for about 10 minutes to five hours.

In another aspect of this invention, the compound of formula VI is reacted with a halogenating agent to obtain the corresponding halo compound of formula I in which $R^1$, $R^2$ and $R^3$ are as defined herein and $R^4$ is chloro or bromo.

The halogenation is readily accomplished using at least one molar equivalent of a halogenating agent, preferably phosphorous oxychloride or phosphorus oxybromide. A suitable inert solvent can be used, for example, benzene, toluene, tetrahydrofuran, chloroform, methylene dichloride and the like, however the preferred method is to conduct the reactipn without a solvent. A temperature of about 0° to 50° C for about ten minutes to five hours is usually sufficient for the halogenation.

In another aspect of this invention, the compound of formula I in which $R^1$, $R^2$ and $R^3$ are as defined herein and $R^4$ is bromo or chloro is readily reduced to the corresponding compound of formula I in which $R^1$, $R^2$ and $R^3$ are as defined herein and $R^4$ is hydrogen. A preferred method for the preparation of the latter compound of formula I comprises: reacting said compound of formula I in which $R^4$ is bromo or chloro with at least one molar equivalent (preferably five to fifty molar equivalents) of an alkali hydroxide, i.e. sodium or potassium hydroxide, in a solvent consisting of water and a lower alkanol, preferably methanol or ethanol; heating the reaction mixture to a temperature from about 50° C to the boiling point of the reaction mixture; adding a molar excess of a reducing agent, i.e., wet Raney nickel; stirring the mixture at the latter temperature for about two to ten hours; and isolating said compound of formula I in which $R^4$ is hydrogen.

If desired, the halo compound of formula I in which $R^1$, $R^2$ and $R_3$ are as defined herein and $R^4$ is chloro or bromo is readily converted to the corresponding compound of formula I in which $R^1$, $R^2$ and $R^3$ are as defined herein and $R^4$ is a radical of formula Y-X wherein Y is NH and X is defined herein or Y is O and X is phenyl. The replacement of the halo in said compound of formula I in which $R^4$ is chloro or bromo is conveniently achieved by reacting the latter compound of formula I with about one to ten molar equivalents of a compound of formula H-Y-X wherein Y is NH and X is as defined herein or Y is O and X is phenyl at a temperature of about 100° to 200° C for about ten to 50 hours. The latter reaction is preferably conducted under an inert atmosphere, for example, nitrogen or argon, with or without a solvent. The solvent can be omitted if the reactants are mutually soluble. Otherwise, suitable solvents include phenol, cresol, xylenol, xylene, glycerol and the like. Particularly useful solvents are phenol and cresol. When phenol is used as a solvent, a separatable mixture of the compounds of formula I in which $R^4$ is a radical of formula Y-X wherein Y is NH and X is defined herein or Y is O and X is phenyl is obtained. The above reaction can be conducted in a sealed reaction vessel if the reagents or solvents are volatile at the temperature necessary for reaction.

In a further aspect of the process of this invention, the compound of formula VI is reacted with about one to five molar equivalents of a proton acceptor in an inert anhydrous organic solvent at about 0° to 50° C for about one-half to five hours. Substantially two to ten molar equivalents of a compound of formula halogen-X in which the halogen is chloro or bromo and X is lower alkyl, 2,2,6,6-tetramethyl-4-piperidinyl or a radical of formula Z-$R^9$ wherein Z and $R^9$ are as defined herein is added and the resulting mixture is stirred at a temperature of about 30° C to the boiling point of the reaction mixture for about 10 hours to 5 days. The product is isolated to give the corresponding compound of formula I in which $R^1$, $R^2$ and $R^3$ are as defined herein and $R^4$ is a radical of formula Y-X wherein Y is O and X is lower alkyl, 2,2,6,6-tetramethyl-4-piperidinyl or a radical of formula Z-$R^9$ wherein Z and $R^9$ are as defined herein.

In the latter reaction a suitable proton acceptor can be selected from those described above for the cyclization of the compound of formula V; the preferred proton acceptor is sodium hydride. The preferred inert anhydrous organic solvent includes a di(lower)alkyl ether or cyclic(lower)alkyl ether, for example, diethyl ether, diisopropyl ether, tetrahydrofuran, dioxane and the like.

The above processes can be followed to prepare related useful compounds having the ring systems illustrated by formulae I, V and VI. For instance, 3,4-dihydro-3,3-dimethyl-9(IH)oxofuro[3,4-b]quinoline-7-carboxylic acid, a compound having the ring systems of formula VI, is useful for the prevention and treatment of allergic conditions in a mammal. A testing method described by I. Mota, Immunology, 7 681(1964) shows that the latter comound inhibits a positive passive cutaneous anaphylactic (PCA) test in the rat at a parenteral dose of 30 mg/kg body weight.

The following examples illustrate further this invention.

EXAMPLE 1

5,6-Dihydro-3,3-dimethyl-4,1-benzoxozonine-2,7(1H,3H)-dione (V; $R^1$ and $R^2$ = $CH_3$, $R^3$ = H)

A solution of the compound of formula II, 1,3,4,9-tetrahydro-1,1-dimethylpyrano[3,4-b]indole (25.7 g, 0.127 M, described in U.S. Pat. No. 3,852,285, issued Dec. 3, 1974), in 587 ml of methanol is added dropwise to a solution of sodium metaperiodate (60.6 g) in 311 ml of water. The solution is stirred at room temperature for 24 hours. The resulting precipitate is collected by filtration washed with methanol and discarded. The filtrate is concentrated under reduced pressure, water is added and the precipitate is collected. The filtrate is extracted with dichloromethane. The organic extract is washed with water, dried and evaporated. The residue is combined with the latter precipitate, dissolved in acetone, treated with charcoal and concentrated to obtain crystals of the title compound, mp 146°–148° C.

Similarly oxidation with ozone, peracids such as perbenzoic acid or peracetic acid, or autoxidation with platinum catalyst and molcular oxygen gives the title compound.

The procedure of Example 1 can be followed to prepare other compounds of formula V in which $R^1$, $R^2$ and $R^3$ are as defined herein. Examples of such compounds are listed in Table 1. In each of these examples an equivalent amount of the appropriate starting material of formula II listed therein is used instead of the starting material of formula II described in the procedure of Example 1.

TABLE 1

| Ex. | Starting Material of Formula II | | | Product: [(prefix listed below)-4,1-benzoxazonine-(suffix listed below)] |
|---|---|---|---|---|
| | $R^1$ | $R^2$ | $R^3$ | Prefix//Suffix |
| 2 | $CH_3$ | $CH_3$ | $CH_3$ | 5,6-dihydro-3,3,6-trimethyl//2,7(1H,3H)-dione; mp 177–178° C |
| 3 | $CH_3$ | $CH_2\overset{O}{\overset{\|}{C}}N(CH_3)_2$ | H | 1,2,3,5,6,7-hexahydro-N,N,3-trimethyl-2,7-dioxo//3-acetamide; mp 164–165° C |
| 4 | $CH_3$ | $(CH_2)_3\overset{O}{\overset{\|}{C}}N(C_2H_5)_2$ | $C_2H_5$ | 1,2,3,5,6,7-hexahydro-3-methyl-N,N,6-triethyl-2,7-dioxo//3-butanamide |
| 5 | $(CH_2)_2CH_3$ | $(CH_2)_2CH_3$ | $(CH_2)_3CH_3$ | 6-butyl-3,3-dipropyl-5,6-dihydro//2,7(1H,3H)-dione |
| 6 | $C_2H_5$ | $(CH_2)_2\overset{O}{\overset{\|}{C}}N(CH_3)_2$ | $(CH_2)_5CH_3$ | 1,2,3,5,6,7-hexahydro-3-ethyl-6-hexyl-N,N-dimethyl-2,7-dioxo//3-propanamide |
| 7 | $CH_2CH(CH_3)_2$ | $CH_2\overset{O}{\overset{\|}{C}}N[CCH_2)_2-CH_3]_2$ | $CH(CH_3)_2$ | 1,2,3,5,6,7-hexahydro-3-(2-methylpropyl)-6-(1-methylethyl)-N,N-dipropyl-2,7-dioxo//3-acetamide |

EXAMPLE 8

3,4-Dihydro-3-dimethylfuro[3,4-b]quinolin-9(1H)-one (VI; $R^1$ and $R^2 = CH_3$, $R^3 = H$)

A solution of the compound of formula V, 5,6-dihydro-3,3-dimethyl-4,1-benzoxazonine-2,7(1H,3H)-dione (11.66 g, described in Example 1), in tetrahydrofuran (250 ml) is added to a stirred mixture of sodium hydride (4.8 g, 55% dispersion) in tetrahydrofuran (220 ml). The mixture is stirred at room temperature for 30 minutes and acetic acid is added until the mixture is neutral. The precipitate is collected and washed with a small amount of tetrahydrofuran and water. The precipitate is dried and crystallized from methanol to give the title compound, mp 335°–340° C (dec.).

In the same manner but replacing sodium hydride with other bases, for instance, n-butyl lithium, sodium hydroxide, potassium carbonate, sodium bicarbonate, sodium ethoxide or potassium t-butoxide, the title compound is obtained.

The procedure of Example 11 can be followed to prepare other componds of formula VI in which $R^1$, $R^2$ and $R^3$ are as defined herein. Examples of the latter componds of formula VI are listed as products in Table 2 together with the appropriate starting material of formula V. In each case the starting material is noted by the number of the example in which it is prepared.

EXAMPLE 15

3,4-Dihydro-1-[dimethylamino)methyl]-3,3-dimethyl-furo[3,4-b]quinolin-9(1H)-one (VI; $R^1$ and $R^2$ — $CH_3$, $R^3 = CH_2N(CH_3)_2$)

A mixtue of 1-(indol-3-yl)-3-(dimethylamino)propan-2-ol [9.5 g, 0.00435 mole, described by Z. G. Starostina et al., Khim.-Farm. Zh., 6, 14(1972) (Chem. Abstr., 78, 58185 r)] and p-toluenesulfonic acid (10 g, 0.0525 mole) in dry acetone (100 ml), is refluxed for 24 hours. The reaction mixture is evaporated and the residue is dissolved in water. The aqueous acidic solution is extracted with diethyl ether and the aqueous phase is basified with a saturated solution of sodium carbonate. The alkaline aqueous phase is extracted with diethyl ether and the organic extract is dried over magnesium sulfate, treated with charcoal and evaporated to give a residue of 3-[(dimethylamino)methyl]-1,3,4,9-tetrahydro-1,1-dimethylpyrano-[3,4-b]indole, a compound of formula II. The hydrochloride salt of the latter compound is crystallized from acetonitrite, mp 213°–215° C.

A solution of the compound of formula II, 3-[(dimethylamino)methyl]-1,3,4,9-tetrahydro-1,1-dimethyl-pyrano[3,4-b]indole (18.3 g, described above) in methanol (300 ml) is added dropwise to a stirred solution of sodium metaperiodate (30 g) in water (300 ml). The reaction mixture is stirred at room temperature for 2 days and filtered. The filtrate is concentrated by evaporation to remove the methanol and the concentrate is extracted with methylene chloride. The organic extract is dried over magnesium sulfate and evaporated. The residue is subjected to chromatography on silica gel

TABLE 2

| Ex. | No. of the Example in which starting material is prepared | Product: [(prefix listed below)-furo[3,4-b]quinoline-(suffix listed below)] Prefix//Suffix |
|---|---|---|
| 9 | 2 | 3,4-dihydro-1,3,3-trimethyl//9(1H)-one |
| 10 | 3 | 1,3,4,9-tetrahydro-N,N-3-trimethyl-9-oxo//3-acetamide, mp 198–199° C |
| 11 | 4 | 3-methyl-1,3,4,9-tetrahydro-N,N-1 triethyl-9-oxo//3-butanamide |
| 12 | 5 | 1-butyl-3,4-dihydro-3,3-dipropyl//9(1H)-one |
| 13 | 6 | N,N-dimethyl-3-ethyl-1-hexyl-1,3,4,9-tetrahydro-9-oxo//3-propanamide |
| 14 | 7 | 1-(1-methylethyl)-3-(2-methylpropyl)-N,N-dipropyl-1,3,4,9-tetrahydro-9-oxo//3-acetamide | using 5% methanol in chloroform. The eluates are evaporated and crystallized from hexane to give the title compound, mp 153°–155° C. The title compound is dissolved in ether and maleic acid is added. The crystals are collected to give the title compound as the maleate salt, mp 197° C.

Similarly oxidation with ozone, peracids such as perbenzoic acid or peracetic acid, or autoxidation using platinum catalyst and molecular oxygen gives the title compound.

The procedure of Example 15 can be followed to prepare other compounds of formula VI in which $R^1$ and $R^2$ are defined herein and $R^3$ is $(CH_2)_mNR^7R^8$ wherein $n$, $R^7$ and $R^8$ are as defined herein. Examples of the latter compounds of formula VI are listed as products in Table 3. In each of these examples an equivalent amount of the appropriate starting material of formula II listed therein is used instead of the starting material of formula II described in the procedure of Example 15.

EXAMPLE 23

9-Chloro-1,3-dihydro-3,3-dimethylfuro[3,4-b]quinoline
(I; $R^1$ and $R^2$ = $CH_3$, $R^3$ = H, $R^4$ = Cl)

A solution of the compound of formula VI, 3,4-dihydro-3,3-dimethylfuro[3,4-b]quinolin-9(1H)-one (6.5 g, described in Example 8), in phosphorus oxychloride (26 ml) is stirred vigorously at room temperature for one hour. The solution is added to 340 ml of crushed ice. The mixture is stirred and the precipitate is removed by filtration. The filtrate is diluted with ice-water (600 ml) and made alkaline with 30% sodium hydroxide solution (75 ml). The precipitate is collected and crystallized from petroleum ether to give the title compound, mp 108°–110° C. The hydrochloride salt of the title compound melts at 189°–194° C.

In the same manner but replacing phosphorus oxychloride with an equivalent amount of phosphorus oxybromide the corresponding compound of formula I in

TABLE 3

| | Starting Material of formula II | | | Product: [(prefix listed below)-furo[3,4-b]quinolin-(suffix listed below)] |
|---|---|---|---|---|
| Ex. | $R^1$ | $R^2$ | $R^3$ | Prefix//Suffix |
| 16 | $C_3H_7$ | $CH_2CN(CH_3)_2$ (with C=O) | $(CH_2)_3N(CH_3)_2$ | N,N-dimethyl-1[3-(N,N-dimethylamino)propyl]-3-propyl-1,3,4,9-tetrahydro-9-oxo//3-acetamide |
| 17 | $C_4H_9$ | $C_2H_5$ | $(CH_2)_4N(C_2H_5)_2$ | 3-butyl-1-[4-(N,N-diethylamino)butyl]-3,4-dihydro-3-ethyl//9(1H)-one |
| 18 | $CH_3$ | $(CH_2)_3CN(C_2H_5)_2$ (with C=O) | $CH_2N[(CH_2)_2CH_3]_2$ | 1-[(N,N-dipropylamino)methyl]-N,N-diethyl-3-methyl-1,3,4,9-tetrahydro-9-oxo//-3-butanamide |
| 19 | $C_2H_5$ | $C_5H_{11}$ | $(CH_2)_6N(CH_3)_2$ | 1-[6-(N,N-dimethylamino)hexyl]-3,4-dihydro-3-ethyl-3-pentyl//9(1H)-one |
| 20 | $CH_3$ | $(CH_2)_5CN(CH_3)_2$ (with C=O) | $CH_2N(CH_3)_2$ | 1-[(N,N-dimethylamino)methyl]-1,3,4,9-tetrahydro-N,N,3-trimethyl-9-oxo//-3-hexanamide |

EXAMPLE 22

1,3-Dihydro-3,3-dimethylfuro[3,4-b]quinolin-9-ol p-toluenesulfonate (I; $R^1$ and $R^2$ = $CH_3$, $R^3$ = H, $R^4$ = p-toluenesulfonate)

The compound of formula VI, 3,4-dihydro-3,3-dimethylfuro[3,4-b]quinolin-9(1H)-one (4.3 g, described in Example 8), is added portionwise to a solution of tosyl chloride (3.8 g) in dry pyridine (50 ml) at 0° C. The solution is stirred at 0° C for 30 minutes and saturated salt solution is added. The mixture is extracted with ether and the ether extract is evaporated. Toluene is added to the residue and the solution is evaporated. The residue is crystallized from methanol to give the title compound, mp 116°–118° C.

In the same manner but replacing the starting material with other compounds of formula VI, then other compounds of formula I in which $R^1$, $R^2$ and $R^3$ are as defined herein and $R^4$ is p-toluenesulfonate are obtained. For instance, replacing the above starting material with the title compound of formula VI described in Examples 10, 12, 13 and 15, the following compounds of formula I are obtained, respectively:

1,3,4,9-tetrahydro-N,N,3-trimethyl-9-[[(4-methylphenyl)sulfonyl]oxy]furo[3,4-b]quinolin-3-acetamide, 1-butyl-1,3-dihydro-3,3-dipropylfuro[3,4-b]quinolin-9-ol p-toluenesulfonate, 3-)3,3-dimethylfutyl)-3-propyl-1,3,4,9-tetrahydro-9-[[(4-methylphenyl)sulfonyl]oxy]-furo[3,4-b]quinolin-3-propanamide and 1-[(N,N-dimethylamino)methyl]-3,3-dimethyl-1,3-dihydro-furo[3,4-b]quinolin-9-ol p-toluenesulfonate.

which $R^1$ and $R^2$ = $CH_3$, $R^3$ = H and $R^4$ =0 Br is obtained.

In the same manner but replacing the starting material with other compounds of formula VI and using either phosphorus oxychloride or phosphorus oxybromide, then other compounds of formula I in which $R^1$, $R^2$ and $R^3$ are as defined herein and $R^4$ is chloro or bromo are obtained. For instance, replacing the above starting material with the title compounds of formula VI described in Examples 10, 12, 13 and 15, the following compounds of formula I are obtained, respectively:

9-chloro-1,3,4,9-tetrahydro-N,N,3-trimethyl-furo[3,4-b]quinoline-3-acetamide, 9-bromo-1-butyl-1,3-dihydro-3,3-dipropyl-furo[3,4-b]quinoline, 9-bromo-N,N,-dimethyl-3-ethyl-1-hexyl-1,3,4,9-tetrahydrofuro[3,4-b]quinolin-3-propanamide and 9-chloro-1,3-dihydro-3,3-dimethyl-1-[(N,N-dimethylamino)-methyl]-furo[3,4-b]quinoline as the maleic acid addition salt, mp 155°–157° C.

EXAMPLE 24

1,3-Dihydro-3,3-dimethyl-1-[(N,N-dimethylamino)methyl]furo[3,4-b]quinoline (I; $R^1$ and $R^2$ = $CH_3$, $R^3$ = $CH_2N(CH_3)_2$ A solution of the compound of formula I, 9-chloro-3,3-dimethyl-1-[N,N-dimethylamino)methyl]-1,3-dihydrofuro[3,4-b]quinoline (10.0 g., described in Example 23), in methanol (100 ml) is added to a solution of sodium hydroxide (20 g) in water (200 ml) and the solution is heated to reflux. Raney nickel (60 g, wet) is added and the mixture is heated at reflux for 6 hours. The mixture is decanted and the catalyst is washed with hot water followed by methanol. The reaction solvents and washings are filtered through diatomaceous earth ("Celite") and the filtrate is concentrated. The residue is extracted with chloroform. The organic extract is dried over magnesium sulfate and evaporated. The residue is subjected to chromatography on silica gel using 5% methanol in chloroform. The eluates are evaporated to give the title compound, nmr (DMSO-D$_6$) δ 1.58 and 1.68 (singlets, 6H), 3.00 (s, 6H), 3.6 (m, 1H), 5.8 (m, 1H), 6.1 (s, 2H), and 7.9 ppm (m, 4H). The maleate salt of the title compound is prepared and crystallized from methanol-ether, mp 185° C.

In the same manner, but replacing the starting material with other compounds of formula I in which R$^4$ is chloro or bromo, then other compounds of formula I in which R$^1$, R$^2$ and R$^3$ are as defined herein and R$^4$ is hydrogen are obtained. For instance, replacing the above starting material with the other compounds of formula I described in Example 23, the following compounds of formula I are obtained: 1,3-dihydro-3,3-dimethyl-1-[N,N-dimethylamino)methyl]furo[3,4-b]quinoline, 1,3,4,9-tetrahydro-N,N,3-trimethyl-furo[3,4-b]quinolin-3-acetamide, 1-butyl-1,3-dihydro-3,3-dipropyl-furo[3,4-b]quinoline- and N,N-dimethyl-3-ethyl-1-hexyl-1,3,4,9-tetrahydro-furo[3,4-b]quinolin-3-propanamide.

EXAMPLE 25

9-[[2-(dimethylamino)ethyl]amino]-1,3-dihydro-3,3-dimethylfuro[3,4-b]quinoline (I; R$^1$ and R$^2$ = CH$_3$, R$^3$ = H, R$^4$ = NH(CH$_2$)$_2$N(CH$_3$)$_2$ A mixture of the starting material of formula I, 9-chloro-1,3-dihydro-3,3-dimethylfuro[3,4-b]quinoline (8.0 g, described in Example 31), phenol (15 g) and the amine of formula H-Y-X, dimethylaminoethylamine (9.8 g), is heated at 150° C for 18 hours under an atmosphere of nitrogen. Ether is added and the reaction is washed with 10% sodium hydroxide solution. The organic phase is extracted with 6N hydrochloric acid and the aqueous phase is washed with ether. The aqueous phase is basified with 10% sodium hydroxide and extracted with ether. The organic extract is washed with water, dried, evaporated and crystallized from ethyl acetate to yield the title compound, mp 126°-127° C. The corresponding hydrochloride salt of the title compound is crystallized from ethanol, mp 182°-190° C.

By following the procedure of Example 25 using the appropriate 9-halofuro[3,4-b]quinoline derivatives of formula I (described in Example 23) and the appropriate amino compound of formula H-Y-X, other compounds of formula I in which R$^4$ is a radical of formula Y-X are obtained. Examples of the latter compounds of formula I are listed as products in Table 4, together with the starting 9-halofuro[3,4-b]quinoline of formula I and the compound of formula H-Y-X used for the preparation of the compound of formula I.

TABLE 4

| | 9-halofuro[3,4,-b]quinoline of formula I | | | | Compound of formula H-Y-X | | Product:[(prefix listed below)-1,3-dihydro-furo[3,4-b]quinoline |
|---|---|---|---|---|---|---|---|
| Ex. | R$^1$ R$^2$ | R$^3$ | R$^4$ | Y | X | | Prefix |
| 26 | CH$_3$ CH$_3$ | H | Cl | NH | (CH$_2$)$_3$N(CH$_3$)$_2$ | | 9-[[3-(dimethylamino)propyl]amino]-3,3-dimethyl, mp 87–88° C; HCl mp 201–240° C |
| 27 | CH$_3$ CH$_3$ | H | Cl | NH | (CH$_2$)$_3$N(C$_2$H$_5$)$_2$ | | 9-[[3-(diethylamino)propyl]amino]-3,3-dimethyl, HCl mp 255–260° C |
| 28 | CH$_3$ CH$_3$ | H | Cl | NH | (CH$_2$)$_2$C$_6$H$_5$ | | 3,3-dimethyl-9-[(2-phenylethyl)amino], HCl mp 151–153° C |
| 29 | CH$_3$ CH$_3$ | H | Cl | NH | CH$_2$CH(OH)-CH$_2$N(C$_2$H$_5$)$_2$ | | 3,3-dimethyl-9-[[3-(diethylamino)-2-hydroxy-propyl]amino], bp 233–235° C/0.03 mm |
| 30 | CH$_3$ CH$_3$ | H | Cl | NH | CH(CH$_3$)(CH$_2$)$_3$-N(C$_2$H$_5$)$_2$ | | 3,3-dimethyl-9-[[4-(diethylamino)-1-methyl-butyl]amino], nmr (CDCl$_3$) δ 0.97 (t, 6H), 1.28 (d, 3H), 1.6 (s, 10H), 2.52 (q, 4H), 3.28 (s, 2H) and 7.8 (m, 4H) and 3,3-dimethyl-9-phenoxy, mp 101–102° C. |
| 31 | CH$_3$ CH$_3$ | H | Cl | NH | (CH$_2$)$_3$—N⟨O⟩ | | 3,3-dimethyl-9-[[3-(4-morpholinyl)propyl]amino], mp 96–98° C, HCl mp 278° C (dec) |
| 32 | CH$_3$ CH$_3$ | H | Cl | NH | (CH$_2$)$_3$—N⟨NCH$_3$⟩ | | 3,3-dimethyl-9-[[3-(4-methyl-1-piperazinyl)-propyl]amino], mp 128–130° C, HCl, mp 245–250° C |
| 33 | CH$_3$ CH$_3$ | H | Cl | NH | (CH$_2$)$_3$N(CH$_2$CH$_2$OH)$_2$ | | 3,3-dimethyl-9-[[3-(di-2-ethanolamino)propyl]-amino], mass spectrum m/e 359, HCl, mp 215–220° C |
| 34 | CH$_3$ CH$_3$ | H | Cl | NH | CH$_2$—⟨pyridyl⟩ | | 3,3-dimethyl-9-[[(3-pyridyl)methyl]amino], HCl, mp 283–289° C |
| 35 | CH$_3$ CH$_3$ | H | Cl | NH | tetramethylpiperidinyl-NH | | 3,3-dimethyl-9-[(2,2,6,6-tetramethyl-4-piperidinyl)amino], mp 200–203° C |
| 36 | CH$_3$ CH$_3$ | H | Cl H | NH | (CH$_2$)$_3$—N⟨2-oxopyrrolidinyl⟩ | | 3,3-dimethyl-9-[[3-(2-oxo-1-pyrrolidinyl)-propyl]amino] |

TABLE 4-continued

| Ex. | 9-halofuro[3,4,-b]quinoline of formula 1 | | | | Compound of formula H-Y-X | | Product:[(prefix listed below)-1,3-dihydro-furo[3,4-b]quinoline |
|---|---|---|---|---|---|---|---|
| | $R^1$ | $R^2$ | $R^3$ | $R^4$ | Y | X | Prefix |
| 37 | $CH_3$ | $CH_2CON(CH_3)_2$ | H | Cl | NH | $(CH_2)_3CH_3$ | 9-butylamino-3-[2-(dimethylamino)-2-oxoethyl]-3-methyl |
| 38 | $CH_3$ | $C_3H_7$ | $C_4H_9$ | Br | NH | $C_6H_5$ | 1-butyl-3-methyl-3-propyl-9-phenylamino |
| 39 | $C_2H_5$ | $(CH_2)_2CON(CH_3)_2$ | $C_6H_{13}$ | Br | NH | $CH_2CH(CH_3)_2$ | 3-ethyl-1-hexyl-3-[[3-dimethylamino)-3-oxopropyl]amino]-9-[(2-methylpropyl)amino] |
| 40 | $CH_3$ | $CH_3$ | $CH_2N(CH_3)_2$ | Cl | NH | $CH_2N(CH_3)_2$ | 3,3-dimethyl-1-(dimethylamino)methyl-9-[[(dimethylamino)methyl]amino] |
| 41 | $CH_3$ | $CH_2CON(CH_3)_2$ | H | Cl | NH | $C_2H_5$ | 3-[2-(dimethylamino)-2-oxoethyl]-9-ethylamino-3-methyl |
| 42 | $CH_3$ | $C_3H_7$ | $C_4H_9$ | Br | NH | 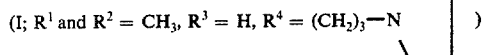 | 1-butyl-3-methyl-3-propyl-9-[[4-(3-pyridyl)-butyl]amino] |
| 43 | $C_2H_5$ | $(CH_2)_2CON(CH_3)_2$ | $C_6H_{13}$ | Br | NH | $(CH_2)_6N(C_2H_5)_2$ | 3-ethyl-1-hexyl-3-[[3-dimethylamino)-3-oxopropyl]amino]-9-[[6-(diethylamino)-hexyl]amino] |
| 44 | $CH_3$ | $CH_3$ | $CH_2N(CH_3)_2$ | Cl | NH | $(CH_2)_2CH(OH)$-$CH_2N[(CH_2)_2CH_3]_2$ | 3,3-dimethyl-1-(dimethylamino)methyl-9-[[4-(dipropylamino)-3-hydroxybutyl]amino] |

EXAMPLE 45

1,3-Dihydro-3,3-dimethyl-9-[[3-(1-pyrrolidinyl)propyl]amino]-furo[3,4-b]quinoline

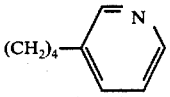

(I; $R^1$ and $R^2$ = $CH_3$, $R^3$ = H, $R^4$ = $(CH_2)_3$—N⟨ ⟩)

A solution of 1,3-dihydro-3,3-dimethyl-9-[[3-(2-oxo-1-pyrrolidinyl)propyl]amino]-furo[3,4-b]quinoline (9.5 g, described in Example 36) in tetrahydrofuran (150 ml) is slowly added to a mixture of lithium aluminum hydride (9.5 g) in tetrahydrofuran (600 ml). The mixture is heated at reflux for 3 hours and cooled. A solution of water-tetrahydrofuran (1:1) is added dropwise and the mixture is filtered. The filtrate is evaporated and a mixture of water-chloroform is added to the residue. The organic phase is separated, dried and evaporated. The residue is subjected to chromatography on a column of alumina (activity II) using acetone-benzene (3:7) as eluant. Evaporation of the eluates and crystallization of the residual oil gives the title compound, mp 70°–75° C. Treatment of the title compound with a solution of hydrogen chloride in ether gives the hydrochloride salt of the title compound, mp 170°–175° C.

EXAMPLE 46

1,3-Dihydro-3,3-dimethyl-9-[2-(dimethylamino)ethoxy]-furo[3,4-b]quinoline (I; $R^1$ and $R^2$ = $CH_3$, $R^3$ = H, $R^4$ =$O(CH_2)_2N(CH_3)_2$)

A solution of the compound of formula VI, 3,4-dihydro-3,3-dimethylfuro[3,4-b]quinolin-9(1H)-one (8.0 g, described in Example 8), in tetrahydrofuran (80 ml) is slowly added over one hour to a suspension of 55% sodium hydride (4 g) in tetrahydrofuran (80 ml) at 20° to 30° C. The mixture is stirred at room temperature for one hour and dimethylaminoethyl chloride (prepared from 20 g of the hydrochloride) is added. The mixture is heated at reflux for 18 hours, filtered and the filtrate is evaporated. The residue is crystallized from acetonitrile to give the title compound, mp 92°–93° C. Treatment of the title compound with a solution of hydrogen chloride in ether gives the hydrochloride salt of the title compound, mp 165°–167° C.

By following the procedure of Example 46 using the appropriate compound of formula Vi and the appropriate compound of formula halogen-X, other compounds of formula I in which $R^4$ is a radical of formula Y-X in which Y is oxygen and X is as defined herein are obtained. Examples of the latter compounds of formula I are listed as products in Table 5 together with the appropriate starting material of formula VI and formula halogen-X. In each case the starting material of formula VI is noted by the number of the example in which it is prepared.

TABLE 5

| Example | No. of the Example in which compound of formula VI is prepared | Compound of formula halogen-X | Product: [(prefix listed below)-1,3-dihydrofuro[3,4-b]quinoline] Prefix |
|---|---|---|---|
| 47 | 8 | Cl—$(CH_2)_3N(CH_3)_2$ | 3,3-dimethyl-9-[3-(dimethylamino)propoxy] mp 71–72° C; HCl salt, mp 179–181° C |
| 48 | 8 | Cl—$CH_2CH(OH)CH_2NHCH(CH_3)_2$ | 3,3-dimethyl-9-[3-[(1-methylethyl)amino]-2-hydroxypropoxy], HCl, mp 175–177° C |
| 49 | 10 | Br—$(CH_2)_2CH(CH_3)_2$ | 3-methyl-3-[2-(dimethylamino)-2-oxoethyl]-9-(3-methylbutoxy) |
| 50 | 12 | Br—$(CH_2)_2C_6H_5$ | 1-butyl-3,3-dipropyl-9-(2-phenylethoxy) |
| 51 | 13 | Cl—$(CH_2)_3$—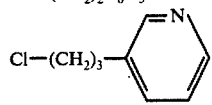 | 3-ethyl-1-hexyl-3-[(2-dimethylamino)-3-oxopropyl] 9-[3-(3-pyridyl)propoxy] |
| 52 | 15 | Cl—$CH_2$—N⟨ ⟩O | 3,3-dimethyl-1-[(dimethylamino)methyl]-9-[(4-morpholinyl)methoxy] |
| 53 | 16 | Cl—$C_2H_5$ | 3-[2-(dimethylamino)-2-oxoethyl]-3-propyl-1-[3-(dimethylamino)propyl]-9-ethoxy |

TABLE 5-continued

| Example | No. of the Example in which compound of formula VI is prepared | Compound of formula halogen-X | Product: [(prefix listed below)-1,3-dihydrofuro[3,4-b]quinoline] Prefix |
|---------|---|---|---|
| 54 | 17 | Cl—(CH$_2$)$_2$—N⟨ ⟩NCH$_3$ | 3-butyl-3-ethyl-1-[4-(diethylamino)butyl]-9-[2-(4-methyl-1-piperazinyl)ethoxy] |
| 55 | 18 | Cl(CH$_2$)$_2$CH(CH$_3$)CH$_2$—N(C$_2$H$_5$)$_2$ | 3-methyl-3-[4-(diethylamino)-4-oxobutyl]-1-[(dipropylamino)methyl]-9-[4-(diethylamino)-3-methylbutoxy] |

We claim:

1. A compound of formula I

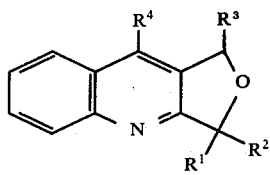

in which R$^1$ is lower alkyl; R$^2$ is lower alkyl; R$^3$ is hydrogen or a radical of formula (CH$_2$)$_n$NR$^7$R$^8$ wherein $n$ is an integer from 1 to 6 and R$^7$ and R$^8$ each is lower alkyl; and R$^4$ is hydrogen, chloro, bromo or a radical of formula Y-X wherein Y is O or NH and X is 2,2,6,6-tetramethyl-4-piperidinyl or a radical of formula Z-R$^9$ wherein Z is lower alkylene or hydroxy (lower) alkylene and R$^9$ is phenyl, 1-pyrrolidinyl, 2-oxo-1-pyrrolidinyl, 3-pyridyl or a radical of formula NR$^{10}$R$^{11}$ wherein R$^{10}$ and R$^{11}$ each is hydrogen, lower alkyl or hydroxy (lower) alkyl, or a therapeutically acceptable salt thereof.

2. A compound of formula I

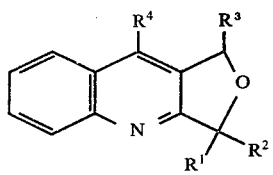

in which R$^1$ is lower alkyl; R$^2$ is lower alkyl; R$^3$ is hydrogen or a radical of formula (CH$_2$)$_n$NR$^7$R$^8$ wherein $n$ is an integer from 1 to 6 and R$^7$ and R$^8$ each is lower alkyl; and R$^4$ is hydrogen, chloro, bromo, or a radical of formula Y-X wherein Y is O and X is a radical of formula Z-R$^9$ wherein Z is lower alkylene or hydroxy (lower) alkylene and R$^9$ is a radical of formula NR$^{10}$R$^{11}$ wherein R$^{10}$ and R$^{11}$ each is hydrogen or lower alkyl, or Y is NH and X is 2,2,6,6-tetramethyl-4-piperidinyl or a radical of formula Z-R$^9$ wherein Z is lower alkylene or hydroxy (lower) alkylene and R$^9$ is phenyl, 1-pyrrolidinyl, 3-pyridyl or a radical of formula NR$^{10}$R$^{11}$ wherein R$^{10}$ and R$^{11}$ each are lower alkyl or hydroxy (lower) alkyl; with the proviso that when R$^1$ and R$^2$ are as defined herein and R$^3$ is a radical of formula (CH$_2$)$_n$NR$^7$R$^8$ wherein R$^7$ and R$^8$ are as defined herein then R$^4$ is hydrogen, chloro or bromo, or a therapeutically acceptable salt thereof.

3. 9-Chloro-1,3-dihydro-3,3-dimethyl-1-[(N,N-dimethylamino)methyl]-furo[3,4-b]quinoline, as claimed in claim 1.

4. 1,3-Dihydro-3,3-dimethyl-1-[(N,N-dimethylamino)methyl]-furo[3,4-b]quinoline, as claimed in claim 1.

5. 9-[[2-(Dimethylamino)ethyl]amino]-1,3-dihydro-3,3-dimethylfuro[3,4-b]quinoline, as claimed in claim 1.

6. 9-[[3-(Dimethylamino)propyl]amino]-3,3-dimethyl-1,3-dihydrofuro[3,4-b]quinoline, as claimed in claim 1.

7. 9-[[3-(Diethylamino)propyl]amino]-3,3-dimethyl-1,3-dihydrofuro[3,4-b]quinoline, as claimed in claim 1.

8. 3,3-Dimethyl-9-[(2-phenylethyl)amino]-1,3-dihydrofuro-[3,4-b]quinoline, as claimed in claim 1.

9. 3,3-Dimethyl-9-[[3-(diethylamino)-2-hydroxypropyl]amino]-1,3-dihydrofuro[3,4-b]quinoline, as claimed in claim 1.

10. 3,3-Dimethyl-9-[[4-(diethylamino)-1-methylbutyl]amino]-1,3-dihydrofuro[3,4-b]quinoline, as claimed in claim 1.

11. 3,3-Dimethyl-9-[[3-(di-2-ethanolamino)-propyl]amino]-1,3-dihydrofuro[3,4-b]quinolne, as claimed in claim 1.

12. 3,3-Dimethyl-9[[(3-pyridyl)methyl]amino]-1,3-dihydrofuro[3,4-b]quinoline, as claimed in claim 1.

13. 3,3-Dimethyl-9[[(2,2,6,6-tetramethyl-4-piperidinyl]amino]-1,3-dihydrofuro[3,4-b]quinoline, as claimed in claim 1.

14. 3,3-Dimethyl-9-[[3-(2-oxo-1-pyrrolidinyl)propyl]amino]-1,3-dihydrofuro[3,4-b]quinoline, as claimed in claim 1.

15. 1,3-Dihydro-3,3-dimethyl-9-[[3-(1-pyrrolidinyl)propyl]amino]-furo[3,4-b]quinoline, as claimed in claim 1.

16. 1,3-Dihydro-3,3-dimethyl-9-[2-(dimethylamino)ethoxy]furo[3,4-b]quinoline, as claimed in claim 1.

17. 3,3-Dimethyl-9-[3-(dimethylamino)propoxy]-1,3-dihydrofuro[3,4-b]quinoline, as claimed in claim 1.

18. 3,3-Dimethyl-9[3-[(1-methylethyl)amino]-2-hydroxypropoxy]-1,3-dihydrofuor[3,4-b]quinoline, as claimed in claim 1.

19. A method for treating hypertension in a mammal which comprises administering to said mammal an effective antihypertensive amount of a compound of claim 1, or a therapeutically acceptable salt thereof.

20. A method for treating microbial infections in a mammal which comprises administering to said mammal an effective antimicrobial amount of a compound of claim 1, or a therapeutically acceptable salt thereof.

21. An antihypertensive composition comprising an effective amount of a compound of claim 1, or a therapeutically acceptable salt thereof, and a pharmaceutically acceptable carrier.

22. An antimicrobial composition comprising an effective amount of a compounds of claim 1, or a therapeutically acceptable salt thereof, and a pharmaceutically acceptable carrier.

* * * * *